United States Patent [19]

Rohowetz et al.

[11] 4,179,397

[45] Dec. 18, 1979

[54] INDICATOR INK

[75] Inventors: Stanley E. Rohowetz, Barrington; Eric Schoenfisch, Palatine, both of Ill.

[73] Assignee: American Can Company, Greenwich, Conn.

[21] Appl. No.: 907,903

[22] Filed: May 22, 1978

[51] Int. Cl.$^2$ .................. C09D 11/10; C08L 61/10; G01N 21/06; G01N 31/00; G01N 31/22; G01N 33/00; G01K 11/16; C09K 3/00

[52] U.S. Cl. .................. 252/408; 23/230 R; 73/73; 73/76; 73/356; 106/22; 116/206; 116/207; 116/216; 260/29.3; 260/32.4; 260/33.4 R; 260/38; 422/26; 422/57; 422/119; 528/137

[58] Field of Search .................. 116/206, 207, 216; 252/408; 73/356, 73, 76; 23/230 R; 106/22, 23; 260/29.3, 32.4, 38, 33.4 R; 528/137; 422/57, 26, 119

[56] References Cited

U.S. PATENT DOCUMENTS

| | | | |
|---|---|---|---|
| 2,798,855 | 7/1957 | Hainsworth | 252/408 |
| 2,798,856 | 7/1957 | Hainsworth | 252/408 |
| 3,078,182 | 2/1963 | Crone, Jr. et al. | 116/207 |
| 3,098,751 | 7/1963 | Huyck et al. | 252/408 |
| 3,288,718 | 11/1966 | Carumpalos | 252/408 |
| 3,360,337 | 12/1967 | Edenbaum | 116/207 |
| 3,386,807 | 6/1968 | Edenbaum | 252/408 |
| 3,390,121 | 6/1968 | Burford et al. | 252/408 |
| 3,523,011 | 8/1970 | Bhiwandker | 252/408 |
| 3,667,916 | 6/1972 | Silva et al. | 252/408 |
| 3,684,737 | 8/1972 | Emigh | 252/408 |
| 3,704,096 | 11/1972 | Verses | 116/207 |
| 3,862,824 | 1/1975 | Chapman | 252/408 |
| 3,898,172 | 8/1975 | Reif et al. | 252/408 |
| 3,905,935 | 9/1975 | Irwin et al. | 106/22 |
| 4,021,252 | 5/1977 | Banczak et al. | 106/30 |
| 4,024,096 | 5/1977 | Wachtel | 106/22 |
| 4,045,397 | 8/1977 | Parkinson | 260/29.3 |
| 4,070,322 | 1/1978 | Hwang | 106/22 |

FOREIGN PATENT DOCUMENTS 1171869 11/1969 United Kingdom .................. 116/206

*Primary Examiner*—Benjamin R. Padgett
*Assistant Examiner*—T. S. Gron
*Attorney, Agent, or Firm*—Robert P. Auber; Ira S. Dorman; Ernestine C. Bartlett

[57] ABSTRACT

An ink composition is provided which is suitable for use on plastic, bare metal, for example, tinplate or aluminum as well as on such metals having organic coatings applied to surfaces thereof. The inks are suitable for use in contact printers or in jet ink printing techniques and apparatus. The ink compositions are thermotropic, i.e. they change color in the presence of water or steam at elevated temperature and are useful as sterilization or pasteurization indicators. The inks comprise essentially a binder resin component, or mixture of such resin components, an alcohol solvent and a combination of dyes which produce a visible and permanent color change in the presence of water or steam at elevated temperatures.

22 Claims, No Drawings

INDICATOR INK

BACKGROUND OF THE INVENTION

1. List of Prior Art

The prior art appears to be best exemplified by the following patents which were developed in a search:

| | | |
|---|---|---|
| Hainsworth | 2,798,855 | July 9, 1957 |
| Hainsworth | 2,798,856 | July 9, 1957 |
| Crone | 3,078,182 | Feb. 19, 1968 |
| Carumpalos | 3,288,718 | Nov. 29, 1966 |
| Edenbaum | 3,360,337 | Dec. 26, 1967 |
| Bhiwandker | 3,523,011 | Aug. 4, 1970 |
| Silva | 3,667,916 | June 6, 1972 |
| Emigh | 3,684,737 | Aug. 15, 1972 |
| Verses | 3,704,096 | Nov. 28, 1972 |
| Chapman | 3,862,824 | Jan. 28, 1975 |
| Banczak | 4,021,252 | May 3, 1977 |
| Wachtel | 4,024,096 | May 17, 1977 |
| Parkinson | 4,045,397 | Aug. 30, 1977 |
| Hwang | 4,070,322 | Jan. 24, 1978 |

2. Field of the Invention

The invention of this application relates to ink jet printing compositions and their use as color change indicators. The compositions are particularly useful as sterilization and/or thermal exposure indicators.

Ink jet printing techniques, although of comparatively recent development in the art of applying decorative and/or identifying indicia to a substrate, are of increasing importance. In general, such techniques impose rigid requirements on the ink compositions. To be suitable for use as a jet ink, the compositions must meet rigid requirements of viscosity and resistivity, solubility, compatibility of components and wettability of substrate; the ink must be quick-drying and smear resistant without clogging the ink jet nozzle and must permit rapid clean-up of the machine components with minimum effort. At the same time, such compositions must also be adapted for satisfactory performance in the particular end use for which they are specifically intended. For example, where the ink is to be employed in the printing of plastic or metal substrates, for example, coated and uncoated tinplate or aluminum, the ink must properly wet the surface and, where the surface is coated, it is highly desirable that some penetration of the coating be effected. In addition to proper wetting and/or penetration of the surface to be printed, the ink must also adhere strongly and be resistant to abrasion or moisture. It has been particularly difficult to obtain satisfactory adhesion and to maintain such adhesion to surfaces which are subjected to sterilization processes involving the combination of moisture and high temperature.

Apart from the jet ink applications of the ink, another area of interest in the art is the provision of printable pasteurization or sterilization indicators. Such compositions have heretofore usually utilized pigment combinations and have been applied primarily in determining whether proper sterilization heat has been applied to objects used in medical and surgical procedures. In the food packaging industry, for example, where metal cans, plastic pouches or coated metal cans are printed, filled with product, sealed and the package subjected to conditions of high temperature and moisture during pasteurization or sterilization techniques, there is a need for such compositions that are printable by either contact or jet ink techniques, that exhibit sufficient adhesion to the substrate to withstand the moisture and high temperature conditions of sterilization and which, at the same time, undergo a visible and permanent color change.

The provision of such an ink composition which shows a distinct difference in color among unsterilized and completely sterilized package provides for ready visible inspection and permits tracing a particular package or packages after they have been processed. The invention thus provides a positive and visible indication that sterilization or pasteurization has in fact been carried out on the product to which the ink is applied.

It is an object of this invention to provide ink compositions, suitable for use in ink jet printing techniques, that exhibit excellent adhesion when exposed to wet immersion or other moisture at elevated temperature conditions and which undergo a visible color change when so exposed.

It is another object of this invention to provide ink compositions, suitable for use in contact printing techniques, that exhibit excellent adhesion when exposed to moisture and elevated temperature conditions and which undergo a visible color change when so exposed.

Yet another object of this invention is to provide ink compositions capable of exhibiting excellent adhesion to both plastic or coated and uncoated metal substrates and which undergo a visible color change when exposed to moisture and high temperature.

These and other objects of the invention will be apparent from the description of the invention which follows.

SUMMARY OF THE INVENTION

This invention relates to a thermotropic ink composition particularly adapted for use as a jet ink composition which comprises a resin binder or combination of such binders, a combination of dyes, a solvent blend and a surfactant. More specifically, the compositions comprise solution compatible resins of the phenol-formaldehyde or resorcinol-formaldehyde class, a dye pair that permits the leaching out or extraction of the more soluble dye at elevated temperature in the presence of steam or water to undergo a visible color change; a solvent blend consisting essentially of a lower alcohol or mixture thereof with methyl or ethyl cellosolve, dimethyl formamide or dimethyl sulfoxide; a surfactant and, optionally, an electrolyte.

DETAILED DESCRIPTION OF THE INVENTION

As described hereinabove, the ink composition of this invention contain an extractible-non-extractible dye combination, a solvent blend, a resinous binder component, a surfactant and other optional components, each of which must be in carefully balanced proportion to achieve successful operation of the ink in a jet printing apparatus and suitable properties as color-change indicators for use on coated and uncoated metal surfaces.

In general, the inks of this invention exhibit the following characteristics for use in ink jet printing systems: (1) a viscosity of about 1–5 cps at ambient temperature; (2) surface tensions for use on metal surfaces of between about 20 and 27 dyne cm. (3) specific resistivity within the range of about 500 ohm cms. to about 1500 ohm cms.

The ink upon application should be water resistant within 30 seconds and dry to the touch within 60 seconds and exhibit a visible color change when exposed to temperatures of at least about 120° F. to about 160° F. and higher.

The Resin Binder

The resins preferred for use herein are best classified as phenolic heat-sensitive resins of the resole type. Such resins include those derived from phenol-formaldehyde, resorcinol-formaldehyde, etc. Suitable resole resins for use herein are solution compatible, alcohol soluble cross-linked polymers or prepolymers having molecular weights within the range of about 1,300 to about 10,000. Such resins are alkaline catalyzed phenol-formaldehyde condensation products in which the ratio of formaldehyde to phenol is greater than one and are usually identified as "B-stage" resins which are curable at elevated temperature by further condensation and/or cross-linking through hydroxymethyl groups to insoluble, chemically resistant, adherent polymers. Such resins are well known in the art. Preferred resins for use herein are commercially available under the trade names BLS-2700 and BKS-2600 from Union Carbide Corp.; Varcum 29108 from Reichold Chemicals; and Methylon 75108 from General Electric. Mixtures of these resins are especially preferred. Such alcohol-soluble binders may be employed as such or they may be modified by admixture with other resins including polyvinyl butyral, polyvinyl acetate, polyacrylics, ethylene-acrylic copolymers, polyamides, etc. In general, the binder will be present in the composition in amounts ranging from about 5 to about 10% by weight and preferably from about 5% to about 8% by weight of the ink composition.

The use of resole phenolic resins, described hereinabove, is believed to be critical to the successful operation of the inks as color-change indicators. It is believed to be essential to the intended result that the resins be such that are susceptible to further curing after application to the substrate under the same conditions by which the dye components function to undergo a color change. Resole phenolic resins as described herein are soluble in the ink solvent, solution compatible with the components of the ink composition and when applied to the substrate undergo further condensation upon subjection to elevated temperature, i.e. above about 120° F., to produce an adherent, insoluble binder for the non-extractible dye component. While the mechanism by which the resin-dye combination functions to convey the desired characteristics to the ink composition is not fully understood, it is believed that while the resin cures under the process conditions with an accompanying release of water, the more soluble or extractible dye is leached out causing a change in color.

If desired, various acidic compounds may be incorporated in the resin component in catalytic amounts to accelerate the resin cure and/or color transition of the composition. Suitable compounds for this purpose include inorganic acids, for example phosphoric acid; esters of such acids, for example dibutyl amino pyrophosphate; organic acids, for example p-toluene sulfonic acid, oxalic acid, etc; metal salts, for example stannous chloride, ferric chloride, etc.

The Dye Combination

Suitable dyes for use in this invention are those which function in combination to undergo a visible and permanent color change when exposed to temperatures above about 120° F. in the presence of moisture. In addition to such color transition characteristics, the dyes must also be soluble in the liquid ink base and be compatible with components thereof.

As contemplated herein, pairs of dyes having differing solubilities or extractibility in water are employed. For example, a specific combination may contain a water soluble blue dye and a relatively water-insoluble red dye in a solvent blend also comprising a resole binder resin. The extractible blue dye is employed in a weight ratio of about 2:1 to the red dye so that markings formed from the composition when applied and dried will be blue. Upon exposure to water at about 120° F. or higher, the substrate color thus changes from blue to a permanent and visible red color. The leaching step which is critical to the successful operation of the invention is not observed when water at temperatures below about 120° F. is employed. Additionally, substantially no change in color or leaching takes place when the resin binder is fully cured or cross-linked. It is believed that the use of resole resins which cure over a period of time with the release of water is critical herein to permit leaching at a satisfactory rate as the products to which the markings are applied are processed.

Particularly good results have been obtained when using Safrinine O as the non-extractible red dye and either of Aniline Blue or Light Green SF as the soluble, leachable blue dyes. Other suitable extractible/non-extractible combinations may be illustrated by permanent dyes selected from the phenylsafranines, Indamine blue or Rhoduline violet dyes; extractible dyes from sodium sulfonate salts of triphenyl methane type dyes such as Food Green #1, Acid Blue #7 or from sodium sulfonate salts of Indulines such as Acid Blue #20, Indulene ZB, etc. It will be obvious that other extractible/non-extractible dye pairs of the same or different color combinations not specifically enumerated hereinabove but of sufficient compatibility, solubility, etc. with the components of the ink composition may be employed.

In general, the dyes will be present in the composition in amounts varying from about 2% to about 5% by weight of the composition with the extractible dye being preferably present in at least A 2:1 ratio by weight of the extractible dye. Alternatively, the dyes may be combined in such proportions that it is unnecessary that one predominant the other in amount. For example, they may blend to form a color which changes upon leaching out the extractible dye.

Ink compositions of the invention have been found to exhibit, for example, a dark blue color upon application to the substrate and to undergo a color change ranging from pink to red after being subjected to a temperature of at least about 120° F. in the presence of water or steam for periods ranging from about 50 to 90 minutes. In general, a readily visible color change will be evidenced in as little as 30 minutes depending on the particular temperature.

The Solvent Blend

Although minor amounts of other solvents may be included in the overall ink composition, the primary solvent is one or more of the lower aliphatic alcohols having 1 to 3 carbon atoms, either individually or in blends thereof. Methanol, ethanol and mixtures thereof are preferred. Additional solvents in which the dyes have a high solubility or which aid in penetrating organic coatings on the substrate may also be included. Certain of the relatively low molecular weight glycol ethers such as ethylene glycol monomethyl ether (methyl cellosolve), and ethylene glycol monoethyl ether (ethyl cellosolve) as well as other more polar solvents such as dimethyl-formamide or dimetyl sulfoxide may also be included. The solvent blend will generally comprise from about 65 to about 97% of the ink composition. The solvent itself may vary from 100% lower alcohol to as little as about 30% alcohol with the remainder of the blend being the auxiliary solvents methyl cellosolve, dimethyl formamide, etc.

Surfactants and electrolytes are optional components that may be added to the compositions of the invention, if desired. Suitable examples of each are anionic and cationic surfactants including sodium lauryl sulfate, alpha methyl sodium lauryl sulfate, fluorinated alkyl esters (commercially available under the trade name of FC-430-from Minnesota, Mining and Manufacturing Co.), FC-430 is the preferred surfactant which may be present in amounts of about 0.01% to about 0.1% by weight. Salts such as lithium chloride or dimethyl amine hydrochloride may be used to improve conductivity. The preferred electrolyte is dimethyl amine hydrochloride which may be present in amounts from about 0% up to about 2% by weight of the composition.

The following examples are illustrative of ink compositions according to this invention which are effective thermotropic jet inks.

EXAMPLE 1

The following compositions were formulated:
Composition A
4% Varcum 29108 phenol-formaldehyde resin
2% BLS-2700 phenol-formaldehyde resin
1% Safranine O
2% Aniline Blue
0.40% phosphoric acid
49% Methanol
41% Dimethyl formamide
0.04% FC-430 surfactant
Composition B
7% BLS-2700 phenol formaldehyde resin
0.80% Safranine O
2% Light Green SF
45% Methanol
45% Dimethyl formamide
0.04% FC-430 surfactant The ink resulting from composition A had a viscosity of 2 cps., a resistivity of 700 ohm cm., and a surface tension of 25 dynes while that of composition B had a viscosity of 3 cps., a resistivity of 1200 ohm cm., and a surface tension of 20 dynes.

Each ink was used in the ink jet printing of bare tinplate and aluminum cans, as well as coated aluminum and tinplate cans and plastic containers. The printed indicia dried very quickly to form blue images displaying excellent adhesion to the substrates. Subjecting the cans to sterilization or pasteurization in the presence of water at 120° F. for 60 minutes or 160° F. for 30 minutes, resulted in a visible color change of the printed indicia from blue to red. Longer time intervals of water immersion up to 8 hours at 160° F. which are typical conditions in meat processing also resulted in a permanent color change.

EXAMPLE 2

Example 1 was repeated except the cans were subjected to water at a temperature of about 100° F. for a period of time ranging up to 120 minutes. No change or transition in color was observed. This example illustrates that the compositions of the invention undergo a color change at an elevated temperature of at least about 120° F., i.e. they function as low-temperature sterilization indicators and do not undergo a color change in the absence of these conditions. It will be seen that this example that merely heating the composition in the absence of water does not cause a color change.

It will also be seen from the above that the compositions of the invention are valuable low-temperature sterilization or pasteurization indicators which can provide multiple functions in the packaging industry. For example, use of the compositions to imprint indicia on metal cans or on plastic ham cans, permits the packager to determine upon visual inspection of any given batch of cans that the containers have been processed at the proper temperature. Additionally, the presence of such visible indicia permits the ready rejection of individual containers that have not been processed and traceability of the origin of the container in the event of defects either in the container or its contents. Additionally, provision of an indicator ink usable in jet printing provides for obtaining the above mentioned character changes and eliminates damage to the containers caused by many of prior contact printing methods.

Finally, because the ink composition is applicable to both coated and uncoated metal substrates and plastic substrates as well they are unusually versatile affording a wide spectrum of suitable substrates on which they may be used.

We claim:

1. An ink composition suitable for use in contact or ink jet printing operations comprising a solution of (a) a soluble resole resin; (b) a combination of dyes of different color wherein one dye is water extractible and the other is relatively water non-extractible; said water extractible dye being present in proportion to said water-insoluble dye in a ratio of at least about 2:1; and (c) a solvent for said resin and dye combination consisting essentially of a lower aliphatic monohydric alcohol or mixture thereof, said composition undergoing a color change upon exposure to water at a temperature of at least about 120° F.

2. An ink composition as claimed in claim 1 wherein said resole resin has a molecular weight within the range of about 1300 to about 10,000.

3. An ink composition as claimed in claim 2 wherein said resole resin is a phenol-formaldehyde or resorcinol-formaldehyde condensation product.

4. An ink composition as claimed in claim 2 wherein said solvent consists essentially of a lower aliphatic monohydric alcohol or mixture thereof with one or more solvents selected from the group consisting of methyl cellosolve, ethyl cellosolve, dimethyl formamide and dimethyl sulfoxide.

5. An ink composition suitable for use in contact or ink jet printing operations comprising a solution of (a) from about 5 to 10% by weight of a soluble resole resin having a molecular weight of about 1300 to 10,000; (b) from about 2% to 5% by weight of a water extractible and water non-extractible pair of dyes of different color; and (c) a solvent for said dyes and resin consisting essentially of a lower aliphatic monohydric alcohol, said ink composition undergoing a color change upon exposure to water at a temperature of at least about 120° F.

6. An ink composition as claimed in claim 5 wherein said resole resin is a combination of phenol-formaldehyde resins, said dye combination is Safranine O/Aniline Blue or Safranine O/Light Green SF and said solvent is methanol.

7. An ink composition as claimed in claim 5 additionally comprising a surfactant.

8. An ink composition as claimed in claim 7 wherein said surfactant is a fluorinated alkyl ester.

9. An ink composition suitable for use in contact or ink jet printing of coated and uncoated metal and plastic surfaces comprising a solution of about 6% phenol formaldehyde resin or mixtures thereof derived from the alkaline catalyzed condensation of phenol and formaldehyde wherein the proportion of formaldehyde to phenol is greater than 1, said resin having a molecular weight within the range of about 1300 to about 10,000; a water extractible-water non-extractible dye pair comprising 1% Safranine O and 2% Aninline Blue, 0.40% phosphoric acid, 49% methanol, 41% dimethyl formamide and 0.04% fluorinated alkyl ester surfactant, said composition undergoing a color change upon exposure to water at a temperature of at least about 120° F.

10. An ink composition suitable for use in contact or ink jet printing of coated and uncoated metal and plastic surfaces comprising a solution of about 7% phenol formaldehyde resin derived from the alkaline catalyzed condensation of phenol and formaldehyde wherein the proportion of formaldehyde to phenol is greater than 1, said resin having a molecular weight within the range of about 1300 to about 10,000; a water extractible-non-extractible dye pair comprising about 0.80% Safranine O and 2% Light Green SF, 45% methanol, 45% dimethyl formamide and 0.04% fluorinated alkyl ester surfactant, said composition undergoing a color change upon exposure to water at a temperature of at least about 120° F.

11. A method of indicating low-temperature sterilization of articles which comprises applying markings to a surface of said articles using a thermotropic ink composition a solution of (a) a soluble resole resin (b) a combination of water extractible and water non-extractible dyes of different color; and (c) a solvent for said resin and dyes consisting essentially of a lower aliphatic monohydric alcohol or mixture thereof; and exposing the marked articles to water at a temperature of at least about 120° F. for a time sufficient to effect a visible color change in said markings.

12. A method as claimed in claim 11 wherein said articles are coated or uncoated tinplate and aluminum cans.

13. A method as claimed in claim 12 in which said resole resin is a phenol-formaldehyde resin having a molecular weight of about 1300 to 10,000.

14. A method as claimed in claim 13 wherein said dye combination is Safranine O/Aniline Blue or Safranine O/Light Green SF.

15. A method as claimed in claim 11 wherein said markings are applied by jet ink printing of said thermotropic ink composition.

16. A method as claimed in claim 11 wherein said markings are applied by contact printing of said thermotropic ink composition.

17. A method of indicating low-temperature sterilization of coated or uncoated tinplate or aluminum or plastic containers which comprises applying markings to a surface of said container using an ink composition comprising a solution of (a) from about 5 to 10% by weight of a soluble phenol-formaldehyde resole resin: (b) from about 2 to 5% by weight of a combination of water extractible and water non-extractible dyes of different color, said extractible dye being present in proportion to said non-extractible dye in a ratio of at least about 2:1; (c) from about 0.01 to 0.1% by weight of a fluorinated alkyl ester surfactant and (d) sufficient amount of a solvent for said resin and dyes to constitute a 100% solution, said solvent consisting essentially of a lower aliphatic monohydric alcohol or mixture thereof;
and exposing the marked containers to water at a temperature of at least about 120° F. for a time sufficient to effect a visible color change in said markings.

18. A method as claimed in claim 17 wherein said extractible dye is Safranine O.

19. A method as claimed in claim 17 wherein said markings are applied by jet ink printing of said ink composition.

20. A method as claimed in 17 wherein said markings are applied by contact printing of said ink composition.

21. A method of indicating low-temperature sterilization of coated and uncoated metal and plastic containers which comprises:
applying markings to a surface of said container using an ink composition comprising a solution of about 6% phenol formaldehyde resin or mixtures thereof derived from the alkaline catalyzed condensation of phenol and formaldehyde wherein the proportion of formaldehyde to phenol is greater than 1, said resin having a molecular weight within the range of about 1300 to about 10,000; a water extractible-water non-extractible dye pair comprising 1% Safranine O and 2% Aniline Blue, 0.40% phosphoric acid, 49% methanol, 41% dimethyl formamide and 0.04% fluorinated alkyl ester surfactant;
and exposing the marked articles to water at a temperature of at least 120° F. for a time sufficient to effect a visible color change in said markings.

22. A method, of indicating low-temperature sterilization of coated and uncoated metal and plastic containers which comprises:
applying markings to a surface of said container using an ink composition comprising a solution of about 7% phenol formaldehyde resin derived from the alkaline catalyzed condensation of phenol and formaldehyde wherein the proportion of formaldehyde to phenol is greater than 1, said resin having a molecular weight within the range of about 1300 to about 10,000; a water extractible-non water-extractible dye pair comprising about 0.80% Safranine O and 2% Light Green SF, 45% methanol, 45% dimethyl formamide and 0.04% fluorinated alkyl ester surfactant,
and exposing the marked articles to water at a temperature of at least 120° F. for a time sufficient to effect a visible color change in said markings.

* * * * *